(12) United States Patent
Du et al.

(10) Patent No.: US 10,758,145 B2
(45) Date of Patent: Sep. 1, 2020

(54) METHOD FOR REALIZING PANORAMIC DISPLAY OF EXERCISE TEST USING TIME AXIS

(71) Applicant: Vales and Hills Biomedical Tech. Ltd., Beijing (CN)

(72) Inventors: Xiaodong Du, Beijing (CN); Yu Yang, Beijing (CN)

(73) Assignee: Vales and Hills Biomedical Tech. Ltd., Beijing (CN)

( * ) Notice: Subject to any disclaimer, the term of this patent is extended or adjusted under 35 U.S.C. 154(b) by 0 days.

(21) Appl. No.: 15/955,726

(22) Filed: Apr. 18, 2018

(65) Prior Publication Data

US 2018/0296109 A1 Oct. 18, 2018

(30) Foreign Application Priority Data

Apr. 18, 2017 (CN) .......................... 2017 1 0252881

(51) Int. Cl.
| | |
|---|---|
| *A61B 5/04* | (2006.01) |
| *A61B 5/044* | (2006.01) |
| *A61B 5/00* | (2006.01) |
| *A61B 5/22* | (2006.01) |
| *A61B 5/0245* | (2006.01) |
| *A61B 5/0432* | (2006.01) |
| *A61B 5/021* | (2006.01) |
| *G16H 50/30* | (2018.01) |

(52) U.S. Cl.
CPC ............ *A61B 5/044* (2013.01); *A61B 5/0245* (2013.01); *A61B 5/0432* (2013.01); *A61B 5/222* (2013.01); *A61B 5/7275* (2013.01); *A61B 5/7435* (2013.01); *A61B 5/021* (2013.01); *A61B 5/02455* (2013.01); *A61B 5/744* (2013.01); *A61B 2503/10* (2013.01); *G16H 50/30* (2018.01)

(58) Field of Classification Search
CPC ..... A61B 5/044; A61B 5/0432; A61B 5/7275; A61B 5/222; A61B 5/0245; A61B 5/7435; A61B 2503/10; A61B 5/02455; A61B 5/021; A61B 5/744; A61B 5/742; G16H 50/30
See application file for complete search history.

(56) References Cited

U.S. PATENT DOCUMENTS

| | | | | |
|---|---|---|---|---|
| 2009/0054743 | A1* | 2/2009 | Stewart .................. | G16H 15/00 600/301 |
| 2016/0360977 | A1* | 12/2016 | Salehizadeh ......... | A61B 5/0245 |
| 2016/0361021 | A1* | 12/2016 | Salehizadeh ......... | A61B 5/0245 |
| 2018/0350451 | A1* | 12/2018 | Ohnemus .............. | G16H 10/60 |

* cited by examiner

*Primary Examiner* — Amanda K Hulbert
*Assistant Examiner* — Natasha Patel
(74) *Attorney, Agent, or Firm* — Bayramoglu Law Offices LLC

(57) ABSTRACT

It relates to the field of displaying the heart-rate data collected in an exercise test, in particular to a method for achieving a panoramic display during Electrocardiogram Exercise Test by using a time axis, comprising following steps: (a) building a horizontal axis (X axis) in units of time as a time axis, and building a vertical axis (Y axis) in units of heart rate, therefore forming a two-dimensional tendency chart; (b) collecting and storing real-time 12-lead ECG raw data, acquiring and storing real-time heart rate data, (c) setting a time vernier, wherein in a default status, the time vernier is located at the current moment, and it is connected with 12-lead ECG raw data.

11 Claims, 2 Drawing Sheets

METHOD FOR REALIZING PANORAMIC DISPLAY OF EXERCISE TEST USING TIME AXIS

CROSS REFERENCE TO THE RELATED APPLICATIONS

The present application is based on and claims priority to the Chinese patent application Ser. No. 201710252881X, filed on Apr. 18, 2017, the entire contents of which are incorporated herein by reference.

TECHNICAL FIELD

The invention relates to the field of displaying the heart-rate data collected in an exercise test, in particular to a method for achieving a panoramic display during Electrocardiogram Exercise Test by using a time axis.

TECHNICAL BACKGROUND

During a traditional electrocardiographic (ECG) exercise test, doctors cannot look back at historical ECG data. They can only see the data at the current moment. Once a doctor misses an abnormal waveform, he cannot retrieve the past data again for analysis during the test. He can only wait until the end of the test, and then analyze the final report. Besides, doctors are not able to see the changing tendency of the heart rate or the changing tendency of the exercise intensity during the test.

SUMMARY OF INVENTION

The present invention aims to solve the following problems.
1. In the prior art, the doctor can only see the heart rate data at the current moment, and cannot retrieve the historical heart rate data in real time.
2. In the prior art, the doctor cannot see the process or the tendency of the heart-rate change.

The technical solution according to the present invention is described in our claim 1 as well as its dependent claims.

The present invention brings the following advantageous effects.
1. The application of the timeline allows doctors to quickly retrieve the ECG data at any past time by operating a time vernier.
2. Through the timeline chart, doctors can see the changing process (change curve) of the heart rate, maybe also the changing process (change curve) of the exercise intensity, maybe also some other data related to the acquisition moment, such as the data of blood pressure at a certain test moment.

DETAILED DESCRIPTION AND EMBODIMENTS

Figure 1:
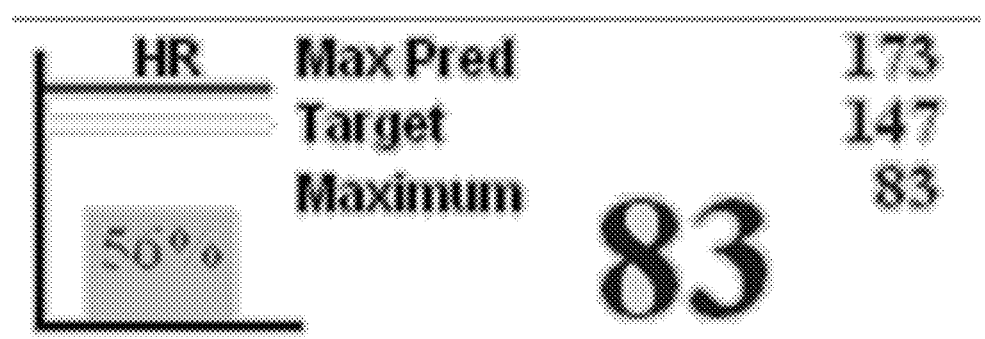
FIG. 1 is a schematic picture showing a prior art of the display of heart rate data during an ECG exercise test. Therein, the number 83 shows the current heart rate (which is the actual heart rate at current moment measured from ECG data), Max Pred is the maximum predicted heart rate (which is calculated on basis of the gender, the age, etc.), Target is the target heart rate (which is calculated from the maximum predicted heart rate), Maximum is the current maximum heart rate (which is the maximum of the actual heart rate up to the current moment in the current test), and 56% in the rectangular block is the percentage of the target heart rate that the current maximum heart rate has reached, i.e. Maximum/Target.

In the present invention, we creatively apply a time axis to an ECG exercise test, which is a development from scratch. It changes the recording process of an ECG exercise test from a single-process recording into a multi-process processing so that the analyzing and the recording may be conducted at the same time.

In our invention, a single ECG exercise test lasts for example for 10-20 minutes.

While the patient is doing exercises (for example, running on a treadmill or pedaling on a pedal exerciser), the software records corresponding ECG data simultaneously.

During an ECG exercise test, the patient should change his exercise intensity according to a predetermined course. For example, the exercise intensity may at the beginning gradually increase. And after reaching a certain predetermined level, the exercise intensity may gradually decrease. ECG signals are acquired at a very high frequency all through the test, including the measurement of blood pressure, for example, the data of blood pressure may be measured at some preset moments. All these data will be serially added to the time axis according to the present invention.

To be specific, our invention provides a method for achieving a panoramic display in Electrocardiogram Exercise Test by using a time axis, comprising the following steps,
(a) building a horizontal axis (X axis) in units of time as a time axis, and building a vertical axis (Y axis) in units of heart rate, therefore forming a two-dimensional tendency chart;
(b) collecting and storing real-time 12-lead ECG raw data, acquiring and storing real-time heart rate data,
(c) adding the real-time heart rate data into the two-dimensional tendency chart as vertical-axis data in correspondence to horizontal-axis time data, thereby forming a real-time tendency chart,
(d) setting a time vernier, which may be for example a vertical line, the time vernier is so configured that it is able to be moved to any history moment,
(e) displaying a corresponding heart rate data in response to the location of the time vernier,
(f) retrieving the past data of 12-lead ECG raw data and displaying the 12-lead ECG raw data corresponding to the location of the time vernier, in response to a request.

Preferably, in the step (a), the unit of the X-axis may be minute or second, and the unit of the Y-axis may be bpm, i.e. beats per minute.

Preferably, the time period along the time axis may be divided into a plurality of levels, corresponding to different exercise-intensity levels.

Preferably, in step (b), the real-time heart rate data are acquired at a frequency of 2 times per second.

Preferably, the data points of the real-time heart rate data in the two-dimensional tendency chart are sequentially connected, to form a dynamical curve showing the changing tendency of the heart rate.

Preferably, in a default state, the time vernier is located at the position of the current time, and is moving forward during the test as time goes on.

Preferably, the time vernier further includes a visualization icon, which is so configured as to visualize the current exercising power and the current exercise-intensity level.

Preferably, the visualization icon may be an animated GIF image or a video, such as a runner, wherein the runner's gait expresses the exercising power, and/or the color of the runner's clothes expresses the exercise intensity. Alternatively, the visualization icon may be an animated GIF image/a video of a cyclist, or other similar icons.

Embodiment 1

Figure 2:
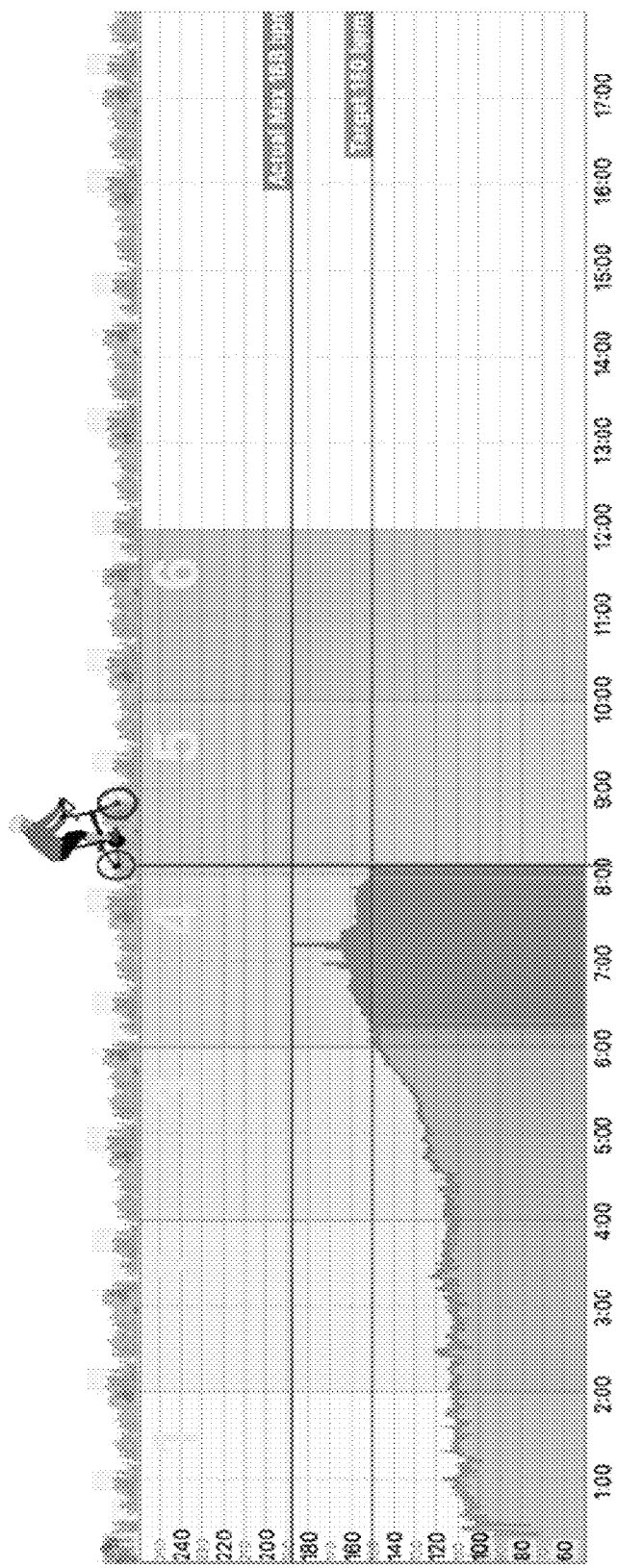
FIG. 2 is a schematic diagram showing the display of heart rate data of an ECG exercise test according to the present invention. Therein, Actual Max 188 bpm is the actual maximum heart rate; Target 150 bpm is the target heart rate.

FIG. 2 shows an embodiment of the display according to the present invention.

FIG. 2 presents a real-time two-dimensional tendency chart according to the present invention. Therein, the X-axis is time, in unit of minute:second. The Y-axis is heart rate, in unit of bpm, i.e. beats per minute.

In our invention, the real-time data are processed into a form of timeline, wherein the ECG data (especially the heart rate data) are spread along the time axis. When the vertical line, which represents the current moment, moves rightward along the horizontal axis, the curve and the shaded region on the left side of the vertical line shows the change of the heart rate during the exercise test.

After the exercise test starts, the software acquires a datum of real-time heart rate every 0.5 seconds as time goes on. The datum obtained each time is imported into the two-dimensional chart as a point with a coordinate of (x, y), wherein x is the time on the horizontal axis, and y is the real-time acquired heart rate. Preferably, a straight line is drawn between every two adjacent heart-rate points, so that a tendency curve of heart rate will appear along the time axis, as time advances.

The vertical axis of the two-dimensional chart is preferably preset from a minimum of 50 beats per minute to a maximum of 180 beats per minute or more than 180 beats per minute, such as 200 beats per minute. This preset range can cover the heart-rate range of most patients. If a very special situation happens such as a heart rate outside this preset range occurs, the vertical axis can be automatically expanded to a new adapted range. FIG. 2 provides such an example. Even though the vertical axis is preset with a maximum of 180 bpm, the actual maximum heart rate has the number of 188 bpm, which extends beyond the preset range, so the vertical axis in the two-dimensional chart is automatically extended to a new range, such as to 220 bpm, 240 bpm or even more.

In our invention, the "actual maximum heart rate" means the maximum of the heart rate actually obtained from the current real-time ECG exercise test. During the ECG exercise test according to our invention, a horizontal line of the actual maximum heart rate may be present in the two-dimensional chart. And every time when a higher heart rate value is acquired, the value of the actual maximum heart rate is replaced by the new higher one, and the horizontal line of the actual maximum heart rate will also simultaneously shift upwards to a new position.

In our invention, the "target heart rate" is the heart rate value that the exercise test desires the patient to achieve. The target heart rate may be calculated on basis of patient's individual information such as age, sex, etc. In our present invention, the target heart rate is presented in the two-dimensional chart as a static horizontal line, which will not change during the test. The relationship with the "actual maximum heart rate" and "target heart rate" can be directly seen from the chart in our invention. Therefore, it can be directly seen whether the target heart rate has been achieved.

Besides, the actual maximum heart rate and the target heart rate are illustrated in FIG. 2, for example with two horizontal lines of different colors. In FIG. 2, the actual maximum heart rate (Actual Max 188 bpm) is marked in blue color together with a blue line located at 188 bpm. The target heart rate (Target 150 bpm) is marked in rot color together with a rot line located at 150 bpm. By comparing the vertical position of the maximum heart rate (the blue line) and/or the current heart rate (the right edge of the shaded region) with the target heart rate (the rot line), it is possible to get some important information at once, such as whether the target heart rate has been achieved, and/or how far it is from the current heart rate to the target heart rate. It is also possible that when the target heart rate has been achieved, the color of the target heart rate as well as its line is changed from rot color into green color.

Further, blood pressure might be also present in the display in real time, so that the doctor can also monitor the change of blood pressure simultaneously.

In our invention, the "time vernier" is an alignment element which is used to be aligned with a point in the time axis, and therefore represents the corresponding time moment. The time vernier in our invention may be presented in a form of a vertical line extending from top to bottom in the tendency chart. In a default status, the time vernier is moving forward along with time, whereas the left of the time vernier represents the past data and the right of the time vernier represents the future.

An important function of the time vernier is that it can be dragged to a certain history moment, so that the historical ECG data at that moment can be retrieved and reviewed in response to a request, for example by double-clicking the mouse, or by clicking a function icon such as "raw ECG data", etc. Some further operations to the historical ECG data may be also possible.

In our invention, since the time axis is synchronized with the 12-lead ECG data, such as the 12-lead electrocardiograms, the ECG raw data (such as the electrocardiogram waveforms, etc.) at any historical moment may be retrieved and reviewed when a user (such as a doctor) drags the vertical line of the time vernier to a certain position along the time axis, for example by using a mouse.

When a doctor monitors a traditional ECG exercise test according to the prior art, it is like watching a movie in a cinema. The audience has no way to look back at a certain segment in the past. However, when a doctor uses the system of the present invention to monitor an ECG exercise test according to our invention, it is like watching a movie on a computer, wherein the user can drag a vernier in a progress bar and thereby choose to retrieve and review any movie fragments as he wishes.

Of course, there are also some difference between a movie on a computer and the present invention. For example, in our invention, there is an over-all display with the changing tendency as well as a selected display of detailed ECG data, while in a movie on a computer there is only one one-dimensional progress bar, rather than a two-dimensional tendency chart in our invention. Moreover, in our invention, it is of course not possible to drag the time vernier into any moment in the future, but only possible to drag the time vernier into a moment in the past.

Preferably, the levels of the exercise intensity may be also shown in the display according to the present invention.

For example, an ECG exercise test may last from 15 to 25 minutes depending on a selected exercise program. As an example, the time period may be evenly distributed on the horizontal axis of the time axis, and be divided into multiple levels (such as levels 1 to 6 in FIG. 2). Each level corresponds to different exercise intensity. In FIG. 2, we use background colors having different saturation to indicate different exercise-intensity levels. When the level of exercise-intensity is higher, the color saturation is also higher. When the level of exercise-intensity is gradually or gradiently increased, the color saturation is also gradually or gradiently increased. For example, the region of the first level is painted with a background color of light pink (low saturation color), and the region of the sixth level is painted with a background color of dark red (high saturation color).

As shown in FIG. 2, the time vernier further includes a visualization icon, to achieve a visual presentation of the current exercise, such as the exercising power and the exercise-intensity level. For example, the visualization icon may be an animated GIF image/a video of a runner, wherein the runner's gait expresses the exercising power. However, the visualization icon is not limited to the form of a runner, but may be an animated GIF image/a video of a cyclist, or other similar icons. In the FIG. 2, the visualization icon is in form of a cyclist.

Embodiment 2

Embodiment 2 is similar to the Embodiment 1.

However, the time vernier is so configured that it is not only able to select a certain time moment, but is also able to select a certain time period in the historical time axis.

For example, the model of "period selection" may be activated by double clicking the mouse when the time vernier is chosen, or by clicking a function icon within/near the two-dimensional chart.

As an illustration example, the time vernier is firstly dragged to (or located at) a first time moment. After that, the mouse is double-clicked and the model of "period selection" is activated. After that, the time vernier is dragged to a second time moment, so that the time period between the first time moment and the second time moment is selected.

As another illustration example, a function icon for "period selection" is clicked by mouse so that the corresponding function is activated. After that, the time vernier is firstly dragged to a first time moment, and then secondly dragged to a second time moment. Thereby, the time period between the first time moment and the second time moment is selected.

After a time period is selected, a request, for example a request of an intermediate report, may be sent to the software. In response to the request, all the raw data of the ECG data during this period such as 12-lead ECG data may be retrieved and be automatically processed, for example to create an intermediate report.

As an example, a selected time period may be a "resting period" (which corresponds to a period wherein the exercise has not started or a period wherein the exercise intensity is the lowest), a "target-heart-rate period" (which corresponds to a period wherein all or most of the actual heart rates therein are higher than the target heart rate), or a "recovery period" (which corresponds to a period wherein the exercise has terminated and/or the patient is recovering from the high-intensity exercises), etc. Due to the interests or the demands of a specific patient or a specific doctor, the time period may be selected as it is demanded.

As an example, an intermediate report might include an averaged electrocardiogram waveform, a changing tendency chart of ST region, ST/HR slop, etc.

In our present invention, the intermediate report might be generated during the test and also after the test.

It is also possible that after the intermediate report for a specific time period is created upon request, the region of the corresponding time period is marked by a specific color and is enclosed by two additional time verniers (located at the start and at the end of the period, respectively). Therewith, the period as well as its intermediate report might be recalled later or edited later. For example, the starting point or the ending point of the period may be moved or adjusted, after the doctor reviewed an intermediate report.

For example, after the test is finished, corresponding intermediate reports for a "resting period", or a "target-heart-rate period", or a "recovery period" may be further edited, and/or may be output as a part of the final report.

Using this embodiment, the function of timeline is emphasized. Thereby, it is possible to analyze a period of test during the exercise test. It has great advantages especially when sometimes the average result (or a maximum value or a tendency chart) during a certain period is of more interest than a single ECG data at a certain moment. Besides, the time vernier along the time axis makes it possible to select a region in a very exact and quick manner. This embodiment also helps to create a better final report with more detailed "period" reports in a very easy way.

Embodiment 3

Embodiment 3 is similar to the Embodiment 1 or 2.

However, an abnormal vernier is added in the Embodiment 3, which may be also a time vernier as a vertical line, but is provided with a warning sign. For example, an icon with a rot exclamatory mark or a rot triangle is provided on the top of the abnormal vernier, in order to attract the doctor's intention.

In our system, it may be preset that an abnormal vernier will be automatically added when one or more predetermined requirements are satisfied. For example, an abnormal condition occurs in the ECG monitoring data, such as the blood pressure is lower than a designated value, or the change of the blood pressure is higher than a predetermined value, or the change of the ST region is more than a predetermined value, etc.

It is possible that the software of our present invention automatically adds an abnormal vernier to a certain time moment, for example when the blood pressure at this moment is lower than a designated value.

It is also possible that the software of our present invention automatically adds an abnormal vernier to a certain time period, for example when the intermediate report is created and comes to the result that there is an abnormal ST region.

It is also possible that the abnormal vernier might be manually added or deleted by the doctor after he reviews the ECG data or the intermediate report.

On one hand, this embodiment automatically marks some abnormal situations and reminds the doctor to pay more attention to the abnormal moments/periods. On the other hand, the embodiment makes it easy to retrieve and recall the data of abnormal moments/periods, which facilitate a further analysis and diagnose of the doctor.

Technical Advantages

All the above embodiments are only illustrative but not limitative. All the modifications or equivalents falling into the scope of the claims are assumed to be covered by our invention.

Last but not least, we summarize some technical advantages of the present invention as follows.

In the past, the doctor in an ECG exercise test can only see the heart rate at the real-time moment, but not able to retrieve any historical data during a real-time monitoring.

Our present invention provides a possibility to retrieve and to recall historical data during the test. It changes the recording process of an ECG exercise test from a single-process recording into a multi-process processing so that the analyzing and the recording may be conducted at the same time during a real-time monitoring.

Besides, using a timer vernier such as a vertical line enables the user to select a time moment and/or a time period in a very easy and very exact way. Thereby, not only the retrieval and analysis of historical 12-ECG raw data becomes very convenient, but also the creation of some intermediate reports or even the creation of a final report regarding one or more designated test periods is significantly facilitated by our invention.

Furthermore, it is possible to use an abnormal time veriner to mark an abnormal situation so that the monitoring and analyzing of abnormal situations is also much easier.

Thereby, the present invention provides a doctor with an over-all view of panoramic tendency chart as well as the possibility to retrieve and further analyze the data at a certain historical time.

These retrieval and analysis during the monitoring would in return help a doctor to react appropriately, for example, to instruct the patient under the exercise test to change the exercise course in real time, for example, to stop the exercise training, to repeat a previous exercise level, to increase/decrease the exercise-intensity level, etc. Thus, the feedback from the retrieval and the intermediate analysis could in turn provide enriched information to the monitoring process and therefore influence the monitoring results, for example, change the exercise course to be carried out. This would help the doctor and the patient to finish an individual exercise test in a more appropriate way.

Besides, since the function of the time vernier can be used not only during a test but also after a test, the convenient selection of the data of a time moment/period, the intermediate reports, as well as the marks of abnormal situations would all help the doctor to finish a final test report in an easier way.

Thereby, using the present invention, a more convenient analysis, a more correct diagnosis, and even an easier test report are achieved.

What is claimed is:

1. A method of analyzing test data during a patient Electrocardiogram Exercise Test (ECG) and displaying the test data collected during the patient Electrocardiogram Exercise Test for achieving a panoramic display in the patient Electrocardiogram Exercise Test by using a time axis, comprising following steps:
   (a) starting the patient Electrocardiogram Exercise Test using software to acquire and record the test data and to build a horizontal axis (X axis) in units of time as a time axis, and to build a vertical axis (Y axis) in units of heart rate and to display the horizontal axis and the vertical axis on a display device, therefore forming a two-dimensional tendency chart;
   (b) collecting and storing real-time 12-lead ECG raw data, acquiring and storing real-time heart rate data,
   (c) setting a time vernier, wherein in a default status, the time vernier is located at the current moment, and the time axis is synchronized with the 12-lead ECG raw data; the time vernier is moved to any history moment during the patient Electrocardiogram Exercise Test, and the heart rate data and the 12-lead ECG raw data at that history moment is retrieved, displayed, and analyzed during the patient Electrocardiogram Exercise Test.

2. The method of claim 1, wherein the time vernier is so configured that it is not only able to select a certain time moment, but also able to select a certain time period in the historical time axis.

3. The method of claim 2, wherein, upon request, all the raw data of the ECG test data in this selected period is retrieved and automatically processed to create an intermediate report.

4. The method of claim 1, wherein an abnormal vernier with a warning sign may be automatically added to the two-dimensional tendency chart, when a preset abnormal condition occurs.

5. The method of claim 4, wherein the abnormal vernier may be manually added or deleted.

6. The method of claim 1, wherein, in the step (a), the unit of the X-axis is minute or second, and the unit of the Y-axis is beats per minute.

7. The method of claim 1, wherein the time period along the time axis is divided into a plurality of levels, corresponding to different exercise-intensity levels.

8. The method of claim 1, wherein, in step (b), the real-time heart rate data are acquired at a frequency of 2 times per second.

9. The method of claim 1, wherein, the data points of the real-time heart rate data in the two-dimensional tendency chart are sequentially connected, to form a dynamical curve showing the changing tendency of the heart rate.

10. The method of claim 1, wherein the time vernier further includes a visualization icon, which is so configured as to visualize the current exercising power and the current exercise-intensity level.

11. The method of claim 10, wherein the visualization icon is an animated GIF image or a video, wherein a runner's gait expresses the exercising power, and/or a color of the runner's clothes expresses the exercise-intensity level.

* * * * *